(12) United States Patent
Gingras

(10) Patent No.: US 9,788,930 B2
(45) Date of Patent: Oct. 17, 2017

(54) SOFT TISSUE IMPLANTS AND METHODS FOR MAKING SAME

(71) Applicant: Proxy Biomedical Limited, Galway (IE)

(72) Inventor: Peter Gingras, Shaker Heights, OH (US)

(73) Assignee: Proxy Biomedical Limited (IE)

( * ) Notice: Subject to any disclaimer, the term of this patent is extended or adjusted under 35 U.S.C. 154(b) by 0 days.

(21) Appl. No.: 13/934,738

(22) Filed: Jul. 3, 2013

(65) Prior Publication Data

US 2014/0178997 A1    Jun. 26, 2014

Related U.S. Application Data

(63) Continuation of application No. 10/621,941, filed on Jul. 17, 2003, now abandoned.

(60) Provisional application No. 60/396,781, filed on Jul. 17, 2002.

(51) Int. Cl.
*A61F 2/00* (2006.01)
*A61F 2/10* (2006.01)
*A61F 2/02* (2006.01)

(52) U.S. Cl.
CPC .......... *A61F 2/0063* (2013.01); *A61F 2/0077* (2013.01); *A61F 2/02* (2013.01); *A61F 2/105* (2013.01); *A61F 2210/0004* (2013.01)

(58) Field of Classification Search
CPC ............... A61F 2/02; A61F 2/00; A61B 17/08
USPC ................... 623/23.72–23.76; 606/151–213; 435/325, 395; 424/422–426
See application file for complete search history.

(56) References Cited

U.S. PATENT DOCUMENTS

| 3,463,158 A | 8/1969 | Scmitt |
| 4,060,081 A | 11/1977 | Yannas et al. |
| RE31,618 E | 7/1984 | Mano et al. |
| 4,787,906 A | 11/1988 | Haris |
| 4,985,036 A | 1/1991 | Lommen et al. |
| 5,011,494 A | 4/1991 | Von Recum et al. |
| 5,356,423 A | 10/1994 | Tihon et al. |
| 5,423,826 A | 6/1995 | Coates et al. |
| 5,468,242 A | 11/1995 | Reisberg |
| 5,512,600 A | 4/1996 | Mikos et al. |

(Continued)

FOREIGN PATENT DOCUMENTS

| EP | 0462426 | 12/1991 |
| WO | WO2004/006808 | 1/2004 |
| WO | WO2004/017869 | 3/2004 |

OTHER PUBLICATIONS

Communication from European Patent Office; Application No. EP 03764798.9; mailed Dec. 13, 2007; (pp. 1-9).

(Continued)

*Primary Examiner* — Yashita Sharma
(74) *Attorney, Agent, or Firm* — Tarolli, Sundheim, Covell & Tummino LLP

(57) ABSTRACT

The present invention features soft tissue implants and methods for making same. The implants can includes a biocompatible film that is rendered porous due to the inclusion of uniformly or non-uniformly patterned cells, and the film has a thickness of less than about 0.015 inches in the event the starting material is non-porous and less than about 0.035 inches in the event the starting material is a microporous film. Multi-film implants can also be made.

14 Claims, 13 Drawing Sheets

(56) References Cited

U.S. PATENT DOCUMENTS

| | | | |
|---|---|---|---|
| 5,634,931 A * | 6/1997 | Kugel | 606/151 |
| 5,658,331 A | 8/1997 | Della Valle et al. | |
| 5,696,175 A | 12/1997 | Mikos et al. | |
| 5,733,337 A | 3/1998 | Carr et al. | |
| 5,766,176 A | 6/1998 | Duncan | |
| 5,885,829 A | 3/1999 | Mooney et al. | |
| 5,980,540 A | 11/1999 | Bruce | |
| 6,071,291 A | 6/2000 | Forst et al. | |
| 6,120,539 A | 9/2000 | Eldridge et al. | |
| 6,136,023 A | 10/2000 | Boyle | |
| 6,162,962 A | 12/2000 | Hinsch et al. | |
| 6,306,079 B1 | 10/2001 | Trabucco | |
| 6,319,264 B1 | 11/2001 | Tormala et al. | |
| 6,328,765 B1 | 12/2001 | Hardwick et al. | |
| 6,355,058 B1 | 3/2002 | Pacetti et al. | |
| 6,425,924 B1 | 7/2002 | Rousseau | |
| 6,432,138 B1 * | 8/2002 | Offray | A61F 2/12 623/8 |
| 6,574,497 B1 | 6/2003 | Pacetti | |
| 6,585,755 B2 | 7/2003 | Jackson et al. | |
| 6,669,706 B2 | 12/2003 | Schmitt et al. | |
| 6,852,330 B2 | 2/2005 | Bowman et al. | |
| 6,966,918 B1 | 11/2005 | Schuldt-Hempe et al. | |
| 7,044,982 B2 | 5/2006 | Milbocker | |
| 7,361,137 B2 | 4/2008 | Taylor et al. | |
| 7,407,699 B2 | 8/2008 | Jacoby | |
| 2003/0114915 A1 | 6/2003 | Mareiro et al. | |
| 2003/0139802 A1 | 7/2003 | Wulfman et al. | |
| 2004/0059356 A1 | 3/2004 | Gingras | |
| 2005/0113849 A1 | 5/2005 | Popadiuk et al. | |
| 2005/0147656 A1 | 7/2005 | McCarthy et al. | |
| 2005/0149032 A1 | 7/2005 | Vaughen et al. | |
| 2005/0214340 A1 | 9/2005 | Erbe et al. | |
| 2005/0261780 A1 | 11/2005 | Heino et al. | |

OTHER PUBLICATIONS

Communication from European Patent Office; Application No. EP 03764798.9; mailed Jul. 30, 2009; (pp. 1-9).
Communication from European Patent Office; Application No. EP 03764798.9; mailed Apr. 13, 2010; (pp. 1-10).
Communication from European Patent Office; Application No. EP 03764798.9; mailed Nov. 25, 2010, (pp. 1-7).
International Preliminary Report on Patentability; Application No. PCT/US2006/035518; mailed Mar. 18, 2008; (pp. 1-7).
International Search Report and Written Opinion issued in PCT/US2006/035518 on Dec. 21, 2006 (12 pages).
International Search Report and Written Opinion; PCT/US2006/035518; mailed Dec. 21, 2006; (pp. 1-12).
International Search Report issued in PCT/US2003/22457 on Dec. 12, 2003.
Response to Office Action, Application No. EP 03764798.9, mailed Oct. 20, 2010; (pp. 1-40).
Response to Office Action, Application No. EP 03764798.9; mailed Jan. 9, 2009; (pp. 1-19).
Response to Office Action, Application No. EP 03764798.9; mailed Feb. 9, 2010; (pp. 1-22).
Response to Office Action; U.S. Appl. No. 12/066, 628; filed Jan. 20, 2012; (pp. 1-7).
Supplementary European Search Report issued in EP03764798 on Aug. 21, 2006.
Supplementary European Search Report issued in EP03764798.9 on Aug. 29, 2006 (3 pages).
USPTO Non Final Office Action; U.S. Appl. No. 12/066,628; mailed Jul. 20, 2011; (pp. 1-11).
Voskerician et al., "Macroporous Condenensed Poly (Tetrafluoroethylene). I. In Vivo Inflammatory Response and Healing Characteristics," J Biomed Mater Res 76A:234-242, 2006.
International Preliminary Examination Report, Application No. PCT/US03/22457, mailed Feb. 13, 2006 (4 pages).

* cited by examiner

Method for Calculating Mesh2 Surface Area

| Area of pore | Ap | 10.89 | mm2 |
|---|---|---|---|
| Perimeter of pore | Pp | 15.08 | mm |
| Thickness | t | 0.20 | mm |
| Area of unit cell | Ac | 31.00 | mm2 |

| Area of space in unit cell | As=Ap+4(Ap/4)=2Ap | 21.78 | mm2 |
|---|---|---|---|
| Top surface area | Atop=Ac-As | 9.22 | mm2 |
| Bottom surface area | Abot=Atop | 9.22 | mm2 |
| Area of thickness | At=t(Pp+4(Pp/4)) | 6.03 | mm2 |

| 3D surface area of a unit cell | Asu=Atop+Abot+At | 24.47 | mm2 |
|---|---|---|---|
| Surface area ratio | Asurf=Asu/Ac | 0.79 | |

Method for Calculating Mesh2C Surface Area

| Area of pore | Ap | 2.78 | mm2 |
|---|---|---|---|
| Perimeter of pore | Pp | 7.83 | mm |
| Thickness | t | 0.20 | mm |
| Area of unit cell | Ac | 7.75 | mm2 |

| Area of space in unit cell | As=Ap+4(Ap/4)=2Ap | 5.56 | mm2 |
|---|---|---|---|
| Top surface area | Atop=Ac-As | 2.19 | mm2 |
| Bottom surface area | Abot=Atop | 2.19 | mm2 |
| Area of thickness | At=t(Pp+4(Pp/4)) | 3.13 | mm2 |

| 3D surface area of a unit cell | Asu=Atop+Abot+At | 7.51 | mm2 |
|---|---|---|---|
| Surface area ratio | Asurf=Asu/Ac | 0.97 | |

Fig. 9B

Method for Calculating Mesh4 Surface Area

| | | | |
|---|---|---|---|
| Area of large pore | Ap | 11.17 | mm2 |
| Perimeter of large pore | Pp | 12.47 | mm |
| Area of small pore | Asm | 2.20 | mm2 |
| Perimeter of small pore | Psm | 8.09 | mm |
| Thickness | t | 0.20 | mm |
| Area of unit cell | Ac | 31.00 | mm2 |

| | | | |
|---|---|---|---|
| Area of space in unit cell | As=Ap+4(Ap/4)+4(Asm/2)=2(Ap+Asm) | 26.74 | mm2 |
| Top surface area | Atop=Ac-As | 4.26 | mm2 |
| Bottom surface area | Abot=Atop | 4.26 | mm2 |
| Area of thickness | At=t(Pp+4(Pp/4)+4(Psm/2))=2t.(Pp+Psm) | 8.22 | mm2 |

| | | | |
|---|---|---|---|
| 3D surface area of a unit cell | Asu=Atop+Abot+At | 16.74 | mm2 |
| 3D surface area per 2D unit cell area | Asurf=Asu/Ac | 0.54 | |

Fig. 10B    Method for Calculating Mesh3 Surface Area

| Area of pore | Ap | 10.89 | mm2 |
|---|---|---|---|
| Perimeter of pore | Pp | 15.08 | mm |
| Thickness | t | 0.20 | mm |
| Area of unit cell | Ac | 35.48 | mm2 |

| Area of space in unit cell | As=Ap+4(Ap/4)=2Ap | 21.78 | mm2 |
|---|---|---|---|
| Top surface area | Atop=Ac-As | 13.70 | mm2 |
| Bottom surface area | Abot=Atop | 13.70 | mm2 |
| Area of thickness | At=t(Pp+4(Pp/4)) | 6.03 | mm2 |

| 3D surface area of a unit cell | Asu=Atop+Abot+At | 33.43 | mm2 |
|---|---|---|---|
| Surface area ratio | Asurf=Asu/Ac | 0.94 | |

SOFT TISSUE IMPLANTS AND METHODS FOR MAKING SAME

The present application is a continuation of U.S. Ser. No. 10/621,941, which was filed on Jul. 17, 2003, which claims the benefit of the priority date of U.S. Ser. No. 60/396,781, which was filed on Jul. 17, 2002. For the purpose of any United States patent that may issue from the present application, the contents of the prior applications are hereby incorporated by reference in their entirety.

TECHNICAL FIELD

This document describes medical devices and relates more specifically to soft tissue implants that can be used to improve injured or otherwise defective tissue within a body.

BACKGROUND

Soft tissue implants are used to reinforce or replace areas of the human body that have acquired defects. The inclusion of biomaterials, which can work either by creating a mechanical closure or by inducing scar formation, has improved the results obtained with soft tissue implants. However, implanting large amounts of synthetic material increases the rate of local wound complications such as seromas (30-50%), paraesthesia (10-20%), and restriction of mobility (25%) (see Klinge et al., *Eur. J. Surg.* 164: 951-960, 1998). Loss of mobility can occur, for example, when soft tissue implants are used in abdominal wall closures. Following implantation, current biomaterials with initially low bending stiffness may turn into hard sheets that cannot be displaced to the same extent as the abdominal wall (i.e., the sheets do not exhibit 25% strain under forces of 16 N/cm (see Junge et al., *Hernia* 5:113-118, 2001)). As a consequence, excessive scar tissue can form, which will decrease mobility in the abdominal wall. In addition, implants can cause inflammation and connective tissue formation. These events appear to be closely related to the amount of material implanted, the type of filament, and the proportion of pores, which define the surface or contact area between the foreign material and the recipient tissues. In particular, large amounts of polypropylene, especially that where the surface has been greatly enlarged by processing multifilaments, induce a strong inflammatory response (see Klosterhalfen et al., *Biomaterials* 19:2235-2246, 1998). Histological analysis of explanted biomaterials has revealed persistent inflammation at the interface, even after several years of implantation. The persistent foreign body reaction is independent of the inflammation time, but considerably affected by the type of biomaterial (see Welty et al., *Hernia* 5:142-147, 2001, and Klinge et al., *Eur. J Surg.*, 165:665-673, 1999). The persistence of this reaction at the biomaterial-tissue interface might cause severe problems, particularly in young patients, in whom the biomaterial is expected to hold for prolonged periods of time.

The are currently several known soft tissue implants. Bard Mesh™ is a non-absorbable implant that is made from monofilament polypropylene fibers using a knitting process (C.R. Bard, Inc., Cranston, R I; see also U.S. Pat. No. 3,054,406; U.S. Pat. No. 3,124,136; and Chu et al., *J. Bio. Mat. Res.* 19:903-916, 1985). Additional non-absorbable meshes are described in, for example, U.S. Pat. Nos. 2,671,444; 4,347,847; 4,452,245; 5,292,328; 5,569,273; 6,042,593; 6,090,116; 6,287,316 (this patent describes the mesh marketed as Prolene™); and U.S. Pat. No. 6,408,656.

The meshes described above are made using synthetic fiber technology. Different knit patterns impart unique mechanical properties to each configuration. The implant surface area ratio has also been calculated for prior art knit biomaterials. The following formulas were used to calculate the surface area ratio:

$$V_{mat} = W_{mat}/D_{mat}$$

where $V_{mat}$ is the material volume, $W_{mat}$ is the material weight, and $D_{mat}$ is the material density which is 0.904 g/cm$^3$ for polypropylene;

$$L_{fiber} = V_{mat}/((\Pi)(R_{fiber})^2)$$

where $R_{fiber}$ is the radius of the fiber and $L_{fiber}$ is the length of the fiber;

$$A_{surface} = (\Pi)(D_{fiber})(L_{fiber})$$

where $A_{surface}$ is the surface area of the fiber used to construct the material and $D_{fiber}$ is the diameter of the fiber; and $$\text{Surface Area Ratio} = A_{surface}/F_{area}$$

where $F_{area}$ is the area of the biomaterial fabric used to obtain $W_{mat}$.

| Product | Construction | Weight (g/cm2) | Fiber Diameter (cm) | Surface Area Ratio |
|---|---|---|---|---|
| Bard Mesh | Monofilament Knit | 0.0096 | 0.017 | 2.52 |
| Trelex Mesh | Monofilament Knit | 0.0112 | 0.017 | 2.65 |
| Prolene Mesh | Monofilament Knit | 0.0096 | 0.015 | 2.91 |

The Gore-Tex Soft Tissue Patch™ is another non-absorbable implant (W.L. Gore & Associates, Inc., Flagstaff, Ariz.; see also U.S. Pat. Nos. 3,953,566; 4,187,390; 5,641,566; and 5,645,915) made from expanded polytetrafluoroethylene (ePTFE). This product is microporous, having pores of approximately 20 microns in diameter. The porosity of the Gore-Tex material may, however, be insufficient to allow incorporation into surrounding tissues; a minimum pore size of approximately 60 microns may be required for fibrous or collagenous material to grow into the patch (Simmermacher et al., *J. Am. Coll. Surg.* 178:613-616, 1994). Methods to improve tissue ingrowth are described in U.S. Pat. Nos. 5,433,996 and 5,614,284, and a method of laminating a layer of mesh-type material to the ePTFE has also been described. In addition, U.S. Pat. No. 5,858,505 describes a macroscopically perforated ePTFE material with perforations having a minimum diameter of about 100 microns, and methods for producing high strength multiple component articles made from ePTFE are described U.S. Pat. Nos. 4,135,093 and 4,478,655, Biomaterials made from ePTFE, however, do not have displacement elasticity properties that would prevent injury at the biomaterial-tissue junction. The ePTFE has a relatively low displacement elasticity, which prevents the biomaterial from extending when physiological force is applied.

Another type of implant, referred to as a "reinforcing plate" has been developed for treating damaged tissues (WO 01/80774). It contains a non-woven material based on polypropylene and forms a plate with small circular perforations (non-woven films may also be described in the art as "biaxially-oriented" films). The plate is preformed in a circular shape for treating damaged tissues of the abdominal wall.

Absorbable soft tissue implants are also known. For example, there are devices composed of polyglycolic acid and non-absorbable filaments (see U.S. Pat. No. 3,463,158; see also U.S. Pat. No. 4,520,821). Absorbable fibers can be use to create a knit mesh (see U.S. Pat. Nos. 4,633,873 and 4,838,884), and a warp knit mesh has been developed to prevent adhesions composed of regenerated cellulose (U.S. Pat. No. 5,002,551). A non-woven mesh made from biodegradable fibers has also been described (U.S. Pat. No. 6,045,908), as has a mesh having two layers that degrade at different rates (U.S. Pat. No. 6,319,264).

The thickness for the commercially available implants disclosed above is provided in the table below. As indicated, the thinnest material available has a thickness of 0.016 inches.

| Material | Company | Code No. | Thickness (inches) |
| --- | --- | --- | --- |
| Bard Mesh | C.R. Bard/Davol | 112660 | 0.026 |
| Prolene Mesh | J&J/Ethicon | PML | 0.020 |
| Gore-Tex Soft Tissue Patch | W.L. Gore | 1415020010 | 0.039 |
| Gore-Tex Soft Tissue Patch | W.L. Gore | 1315020020 | 0.079 |
| ProLite | Atrium Medical | 1001212-00 | 0.019 |
| ProLite Ultra | Atrium Medical | 30721 | 0.016 |

Each of the implants presently in use has one or more deficiencies. For example, their construction can result in characteristics (e.g., wall thickness and surface area) that increase the risk of an inflammatory response or of infection; seromas can form postoperatively within the space between the prosthesis and the host tissues; due to material content, width, and wall thickness, surgeons must make large incisions for implantation (the present implants can be difficult to deploy in less invasive surgical methods); rough implant surfaces can irritate tissues and lead to the erosion of adjacent tissue structures; adhesions to the bowel can form when the implant comes in direct contact with the intestinal tract; where pore size is reduced, there can be inadequate tissue ingrowth and incorporation; and the pore size and configuration of the implants does not permit adequate visualization through the implant during laparoscopic procedures. Accordingly, there remains a need for implants for repairing soft tissue and methods of making those implants.

SUMMARY

The present invention features a soft tissue implant that includes a biocompatible film that is rendered porous due to the inclusion of uniformaly or non-uniformly patterned cells (i.e., the film can contain a plurality of cells); the film has a thickness of less than about 0.015 inches in the event the starting material is non-porous and less than about 0.035 inches in the event the starting material is a microporous film. The terms "porous," "non-porous," and "microporous" are used herein in a manner consistent with their usual meaning in the art (as noted above, the ePTFE material described in U.S. Pat. No. 5,858,505 is a microporous material having perforations with a minimum diameter of about 100µ; the Gore-Tex Soft Tissue Patch™ is made from ePTFE and has pores that are approximately 20µ in diameter). The methods used to make an implant from a non-porous material can be applied to make an implant from a microporous material (and vice-versa), and implants made from either type of starting material can be similarly used to treat patients.

The overall thickness of the implant can remain within the parameters given for the thickness of the individual films (i.e., the soft tissue implant can be less than about 0.015 inches when constructed from one or more non-porous films and less than about 0.035 inches when constructed from one or more microporous films) or it can be a multiple of the individual film's thickness (e.g., where two 0.008" films are laminated, the implant can be about 0.016" thick; where three such films are laminated, the implant can be about 0.024" thick, and so forth). Thus a given implant can include more than one film (e.g., more than one biocompatible film, regardless of whether the starting material is non-porous or microporous; one or more additional films of different content, as described further below, can also be included).

In one embodiment, the invention features a soft tissue implant that includes a first porous biocompatible film and a second porous biocompatible film, the thickness of the implant being less than about 0.015 inches (e.g., about 0.014", 0.013", 0.012", 0.011", 0.010", 0.009", 0.008", 0.007", 0.006", 0.005", 0.004", 0.003", 0.002", 0.001") (as noted above, the thickness of the implant can be less than about 0.035" when microporous films are used (e.g., about 0.033, 0.030, 0.027, 0.025, 0.023, 0.020, 0.018, or 0.015"), and implants containing laminated films will be about as thick as the combined thickness of the incorporated films). The implants, including the materials from which they are made and the cell patterns they can contain are described further below. We note here that, regardless of the number, size, or pattern of the cells within the implants, one or more (and up to all) of the edges of the cells can be atraumatic (i.e., the implant can have cells with smooth, tapered, or rounded edges). The term "cell(s)" may be used interchangeably below with the term "pore(s)."

The soft tissue implants can also have one or more of the material characteristics described below. For example, a soft tissue implant can have a surface area ratio of about 1.5 or less (e.g., of about 1.00 (e.g., 0.90-0.99 (e.g., 0.94 or 0.97)) of about 0.80 (e.g., 0.75-0.79 (e.g., 0.79)) or of about 0.50 (e.g., of 0.45-0.55 (e.g., 0.54))). In addition, or alternatively, the soft tissue implant can be defined by the extent to which it can be distended when placed on or within a body. For example, in some embodiments, the implants can be distended by about 25% or more (e.g., 20%, 30%, 33%, 35%, 40%, 50% or more) at a force borne by a tissue (e.g., a muscle or muscle group) by which they are placed. For example, the implants can be distended by about 25% at 16 N/cm.

The films can be made from a variety of polymers (including absorbable and non-absorbable polymers, such as those set out below) or copolymers thereof. For example, the implants of the invention can include films of non-absorbable polymers such as polypropylene, polyethylene terephthalate, polytetrafluoroethylene, polyaryletherketone, nylon, fluorinated ethylene propylene, polybutester, or silicone. Where absorbable polymers are used, they can be, for example, a polyglycolic acid (PGA), a polylactic acid (PLA), polycaprolactone, or polyhydroxyalkanoate.

The invention also features implants containing biological materials rather than, or in addition to, the polymer-based films described herein. These biological materials may or may not be polymeric. For example, one or more of the films in the implants of the invention can include collagen (which is generally considered to be a repetitive, polymeric substance) or tissue-based products (which are generally not considered to be polymeric). For example, the implants of the invention can be made from films consisting of, or that include, mucosal tissue (e.g., the mucosa and/or submucosa of an organ such as the large or small intestine (the mucosa and/or submucosa can be from a human (as might be obtained from a cadaver) or non-human animal (such as a pig, sheep, cow, goat, horse, or other such animal)). For example, the implants of the invention can be made from porcine submucosa (such as is sold by Cook Surgical (Bloomington, Ind.) as Surgisis™). Films of biological material, such as the mucosal/submucosal preparations described here, can be layered to produce an implant of the invention. As few as two, or as many as 5, 10, 15, 20, or 25 biological films can be adhered to one another and then rendered porous by the same methods (e.g., laser ablation, die punching or other physical intervention) used to introduce a cellular pattern into the conventional polymeric films described herein. As with any of the implants of the invention, the cellular pattern can be regular or irregular and can be repeated in a regular or irregular pattern, an edge of the pores can be smooth, and one or more portions of the periphery of the implant can be reinforced (e.g., can be made thicker or more dense) to facilitate implantation.

The invention also features methods for producing soft tissue implants and methods of using those implants to treat a patient who has an injured or otherwise defective tissue. These methods can include the steps of extruding a biocompatible polymer into a film and forming pores in the film. In alternative embodiments, the film can be stretched or otherwise manipulated (e.g., trimmed, shaped, washed or otherwise treated) before or after forming pores in the film. For example, in one embodiment, the invention features a method having one or more of the following steps: (a) providing a polymeric film or a film of a biological tissue or extruding a polymer into a film; (b) stretching the film (this may be done along one axis or, to the same, similar, or dissimilar extents, along two axes (i.e., biaxially) (stretching the film is less likely to be necessary where the film comprises non-polymeric biological tissue, such as submucosal tissue); (c) laminating one or more films (this is an optional step that can be done by, for example, applying heat, pressure, or an adhesive to two or more films); (d) producing a plurality of cells within the film or laminated films; (e) cleaning the porous implant; and (f) packaging the porous implant. The implant can be sterilized (according to methods known to the art as effective in sterilizing implants and medical devices), before or after it is packaged. The packaged implants, provided, optionally, with instructions for their use are also within the scope of the invention. More specifically, where an implant contains more than one film, the methods of the invention can be carried out by, for example, extruding a first biocompatible polymer to form a first film, extruding a second biocompatible polymer to form a second film, attaching the first film to the second film to produce a soft tissue implant, and forming pores in the soft tissue implant. Alternatively, the pores can be formed before the two films (or any of the multiple films) are adhered to one another. In that instance, the method of making the soft tissue implant can be carried out by, for example: extruding a first biocompatible polymer to form a first film; forming pores in the first film; extruding a second biocompatible polymer to form a second film; forming pores in the second film; and attaching the first film to the second film to produce a soft tissue implant. Implants having two or more films (which may or may not consist of the same material(s)), including those made by the methods described herein, are within the scope of the invention. Thus, the invention features a soft tissue implant made by a method described herein.

Where more than two films (e.g., three, four, five, six, or more) are present, the extruding step can be repeated for each film, and pores can be formed in each film before or after it is incorporated in the implant or adhered to another film. The films in a multi-film implant may be substantially identical or non-identical. For example, they can vary in thickness, length, or width, or in any combination of thickness, length, and width, from one another. The films can also vary in their material content and the size, number, or arrangement of their pores (e.g., an implant can include a tear resistant substrate and the polymers used to construct the film(s) can be compounded with impact modifiers).

As indicated above, as an alternative to forming a film by polymer extrusion, one may simply obtain the film(s). Such films may have substantially final overall dimensions (e.g., substantially final length, width, and thickness) or they may be modified to attain the desired form.

Where a film is obtained, rather than made, the methods of making the soft tissue implant can simply require providing a given film that is then attached (e.g., reversibly or irreversibly bound by mechanical or chemical forces)), if desired, to another film and/or processing the film to alter its outer dimensions (e.g., to decrease, in a regular or irregular way, the length or width of the film; this can be achieved by stretching the film, which may also alter its thickness). The method can continue by processing the film to include one or more pores (or cells) of a given size and arrangement. For example, the single provided film (or adherent multiple films) can then be subjected to a process (e.g., laser ablation, die punching, or the like) that forms pores within the film(s). Accordingly, any of the methods of the invention can be carried out by providing a given biocompatible film, rather than by producing it by an extrusion or extrusion-like process.

The film(s) can be further modified so that the edges, or selected points along the edges, have different features than the remainder of the implant. For example, the implant can be denser along its outer periphery, or at one or more points around the periphery, in order to facilitate suture (or similar fastener) retention (as loss of attachment can cause the implant to fail).

The soft tissue implants of the invent ion may be referred to herein as "non-woven." The term "non-woven" indicates that the implant is made, at least in part, from a material or materials that are processed into sheets or films using traditional melt or paste extrusion methods. After extrusion, the sheet or film can be cut, stretched, annealed, or sintered to change its material properties (preferably in a way that improves the performance of the implant in the body). Before it is machined (by, for example, a laser or other device capable of forming pores within the sheet, or film) the material (i.e., the intact sheet or film) is substantially impermeable (thus, by way of the methods of the invention, non-porous or microporous film can be made into porous implants).

As noted above, the soft tissue implants of the invention can include (or consist of) a film that has low profile (or reduced wall thickness) and that is biocompatible. A biocompatible film is one that can, for example, reside next to biological tissue without harming the tissue to any appreciable extent. As noted above, the film(s) used in the soft tissue implants of the invention can have pores or cells (e.g., open passages from one surface of a film to another) that permit tissue ingrowth and/or cellular infiltration.

The overall shape of the implants can vary dramatically depending on the indication or intended use. The overall length and width of the implants of the present invention can be the same as, or similar to, those of presently available implants (although, of course, other parameters or characteristics, as described herein, will vary). The implants of the invention can be, for example, rectangular in shape. For example, the implants can have a length that is approximately 2, 3, 4, or more times greater than their width. For example, implants having a length that is approximately four times greater than their width can be, for example, about 0.5 cm×2.0 cm (or 0.5"×2.0"); about 1.0 cm×4.0 cm (or 1.0"×4.0"); about 2.0 cm×8.0 cm (or 2.0"×8.0"); about 2.5 cm×10.0 cm (or about 2.5"×10.0"); about 3.0 cm×9.0 cm (or 3.0"×9.0"); etc. Alternatively, the implants can be square, (e.g., they can be 1, 2, 3, 4, 5, 6, 7, 8, 9, 10, 11, or 12 $cm^2$, or 1, 2, 3, 5, 6, 7, 8, 9, 10, 11, or 12 inches square). Larger implants can be readily made and used if required. For example, implants that are about 15.0 cm×15.0 cm; about 20.0×20.0 cm; about 30.0×30.0 cm; or about 45.0×45.0 cm can be made by the methods described herein and are within the scope of the present invention. Of course, round, oval, or irregularly shaped implants may be made as well.

The implants of the present invention offer a combination of high porosity, high strength, and low material content, and they may have one or more of the following advantages. They can include pores or porous structures that stimulate fibrosis and reduce inflammation; they can reduce the risk of erosion and formation of adhesions with adjacent tissue (this is especially true with implants having a smooth surface and atraumatic (e.g., smooth, tapered, or rounded) edges; their displacement elasticity can reduce the damage that may occur with other implants at the tissue-biomaterial interface; they can simulate the physical properties of the tissue being repaired or replaced, which is expected to promote more complete healing and minimize patient discomfort; their surface areas can be reduced relative to prior art devices (having a reduced amount of material may decrease the likelihood of an immune or inflammatory response). Moreover, implants with a reduced profile can be introduced and/or implanted in a minimally invasive fashion, as they are pliable, they can be placed or implanted through smaller surgical incisions. The methods of the invention may also produce implants with improved optical properties (e.g., implants through which the surgeon can visualize underlying tissue). Practically, the micromachining techniques that can be used to produce the implants of the present invention are efficient and reproducible. The soft tissue implants described herein should provide enhanced biocompatibility in low profile configuration while maintaining the requisite strength to repair tissue.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1A is of a polypropylene mesh (Bard Mesh™); FIG. 1B is of Prolene™ Mesh; and FIG. 1C is of Trelex™ Mesh.

FIG. 6A is a diagram of an exemplary pore; structures and areas that can be measured are shown. FIG. 6B is a Table assigning values to various measured parameters within Mesh2 and the equations used to calculate the surface area ratio.

FIG. 7A shows a histological preparation of Mesh2 stained with hematoxylin and eosin, following a 14-day implantation. FIG. 7B shows a histological preparation of Mesh2, Masson's trichrome-stained, following a 14-day implantation.

FIG. 8A is a diagram of an exemplary pore. FIG. 8B is a display of various measured parameters within Mesh 2C and the equations used to calculate the surface area ratio.

FIGS. 9A and 9B relate to a non-woven soft tissue implant designated Mesh4. FIG. 9A is a diagram of an exemplary pore. FIG. 9B is a display of various measured parameters within Mesh4 and the equations used to calculate the surface area ratio.

FIGS. 10A and 10B relate to a non-woven soft tissue implant designated Mesh3. FIG. 10A is a diagram of an exemplary pore. FIG. 10B is a display of various measured parameters within Mesh3 and the equations used to calculate the surface area ratio.

DETAILED DESCRIPTION

Figure 1A:
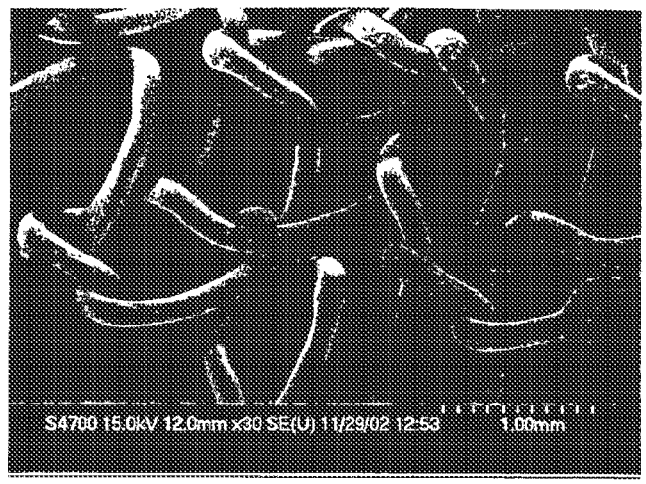
FIGS. 1A-1C are micrographs of commercially available meshes.
Figure 1B:
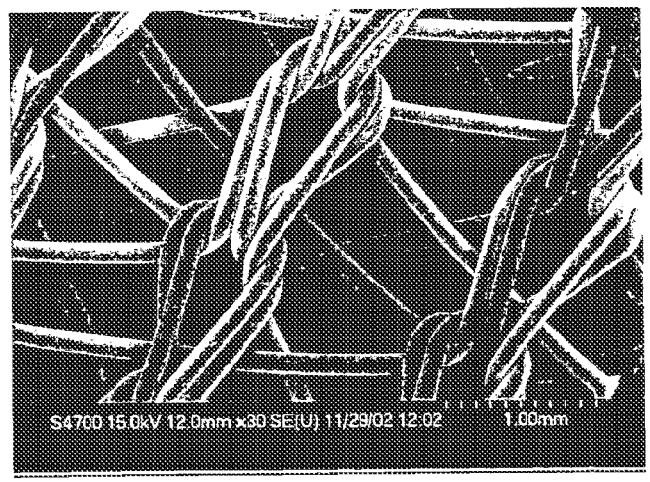
Figure 1C:
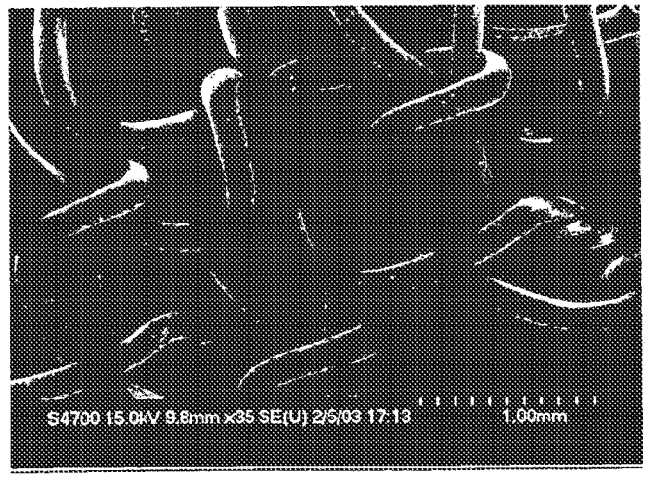
Figure 2A:
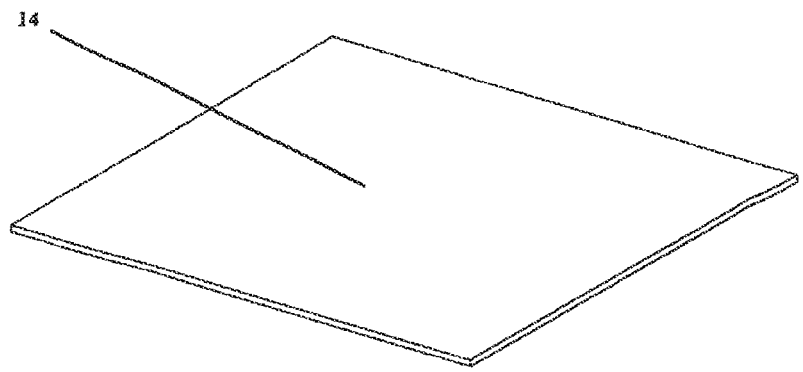
FIGS. 2A-2C are perspective views of materials that can be machined to produce implants of the invention.
Figure 2B:
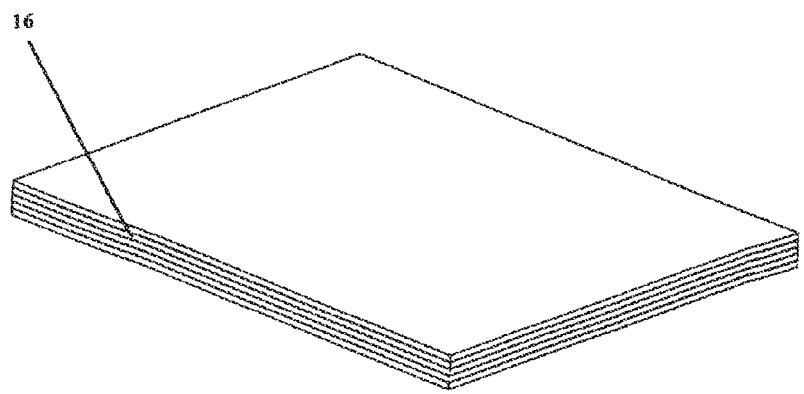
Figure 2C:
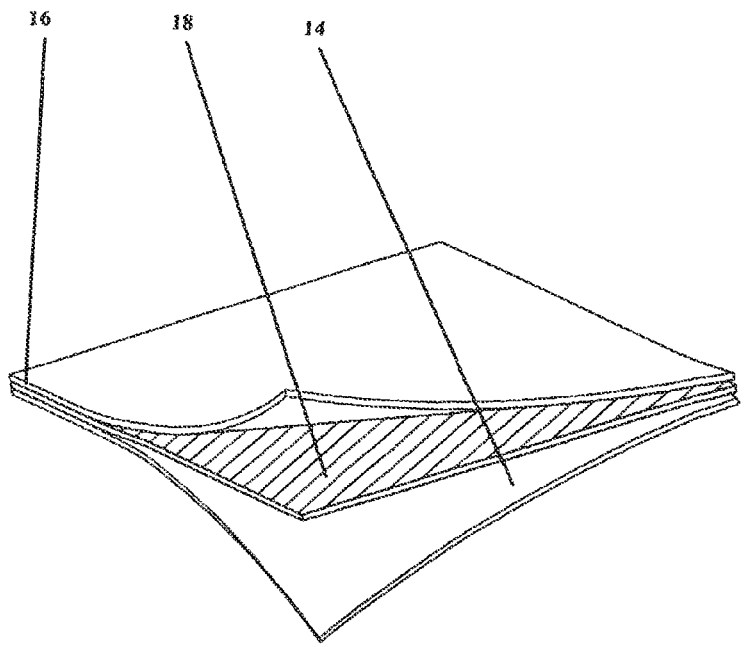

Commercially available, woven materials that have been used to help repair soft tissue are illustrated in FIGS. 1A-1C. The polypropylene mesh shown in the micrograph of FIG. 1A is Bard Mesh, a non-absorbable, knitted material produced by C.R. Bard, Inc. (Murray Hill, N.J.); and the material shown in the micrograph of FIG. 1B is Prolene™ Mesh (Ethicon, Inc., Somerville, N.J.); and the material shown in the micrograph of FIG. 1C is Gore-Tex Soft Tissue Patch™, a non-absorbable implant of ePTFE produced by W.L. Gore & Associates, Inc, (Flagstaff, Ariz.);

FIGS. 2A-2C are perspective views of materials that can be machined to produce a non-woven soft tissue implant of the present invention. FIG. 2A is a perspective view of non-woven biocompatible film 14. Film 14 has known or discernable dimensions (width, length, and thickness), which can be modified or left intact in the manufacture of a soft tissue implant. Film 14 is a single-layer, smooth-edged film. As shown in FIG. 2B, film 14 can be laminated to produce film 16, which can also be used, with or without further modification, to manufacture the implants of the present invention. Multiple layers of biocompatible film 14 can be added together to improve the mechanical properties (e.g., tear resistance or burst strength) of the implant. A first film 14 can be thermally bonded to a second film 14 using hydraulic presses such as those manufactured by OEM Press Systems (Orange, Calif.).

As shown in FIG. 2C, an implant can include laminated film 16, that includes two pieces of film 14 and tear resistant substrate 18. Tear resistant substrate 18 is placed between a first film 14 and a second film 14. Where tear resistant substrate 18 is thermally compatible with film 14, tear resistant substrate 18 and film 14 can be bonded using heat and/or pressure. If necessary, an adhesive or thermal attachment layer can be used between film 14 and tear resistant substrate 18. This may include a layer of material with a lower melting point, which can be achieved by reducing the crystallinity of a like material or by selecting a different material composition. Alternatively, tear resistant substrate 18 can be mechanically bonded to film 14 by sutures, clips, or the like.

Biocompatible materials useful in film 14 or laminated film 16 can include non-absorbable polymers such as polypropylene, polyethylene, polyethylene terephthalate, polytetrafluoroethylene, polyaryletherketone, nylon, fluorinated ethylene propylene, polybutester, and silicone, or copolymers thereof (e.g., a copolymer of polypropylene and polyethylene); absorbable polymers such as polyglycolic acid (PGA), polylactic acid (PLA), polycaprolactone, and polyhydroxyalkanoate, or copolymers thereof (e.g., a copolymer of PGA and PLA); or tissue based materials (e.g., collagen or other biological material or tissue (e.g., mucosal or submucosal tissue) obtained from the patient who is to receive the implant or obtained from another person (e.g., a recently deceased person) or an animal (i.e., the implant can constitute a xenograft)). The polymers can be of the D-isoform, the L-isoform, or a mixture of both. An example of a biocompatible film 14 suitable for producing the laminated film structure 16 is biaxially oriented polypropylene. AET Films (Peabody, Mass.) manufactures biaxially oriented films (AQS and OPB).

Tear resistant substrate 18 can be spun bonded polypropylene, ePTFE, or a polymeric film compounded with impact modifiers.

Figure 3A:
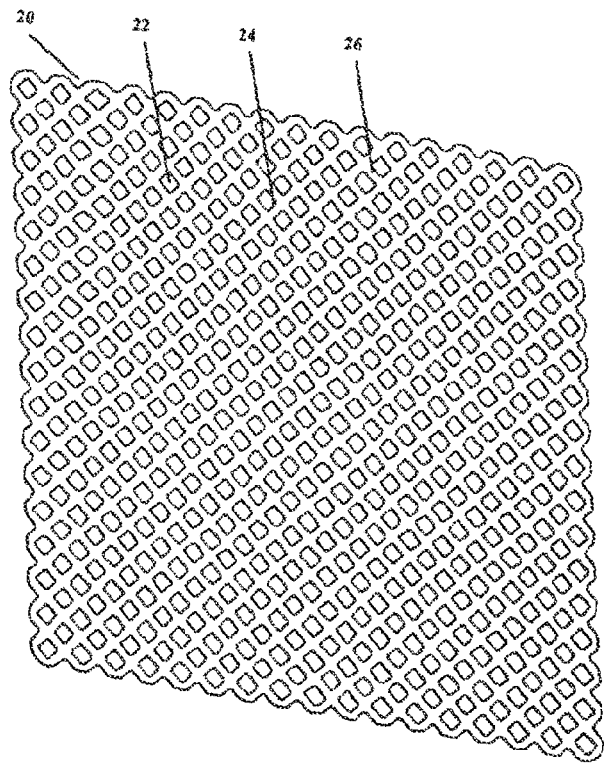
FIGS. 3A and 3B are perspective views of diamond-like cell patterns machined in films.
Figure 3B:
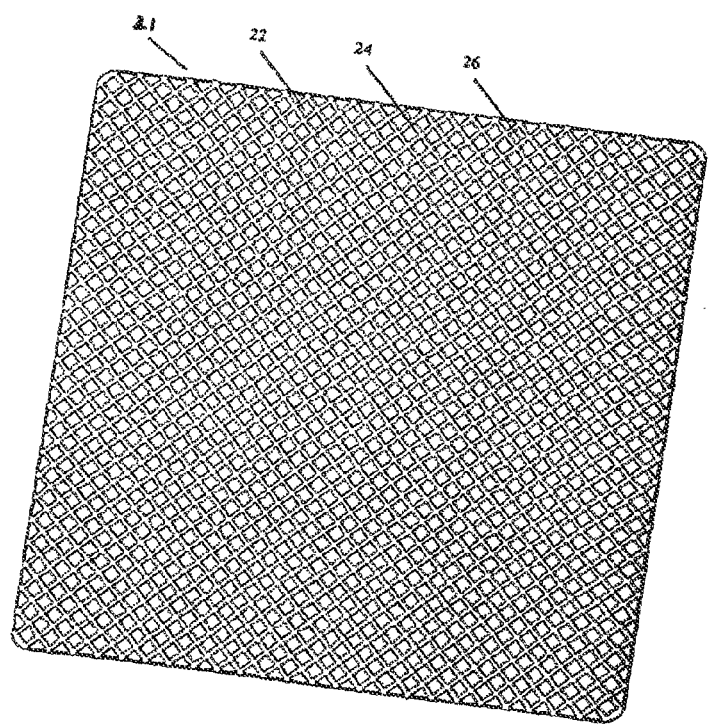

FIGS. 3A and 3B are perspective views of machined films 20 and 21, respectively. Referring to FIG. 3A, diamond-like cell pattern 22 has been machined into film 20 to impart porosity, which can support tissue ingrowth on high strength thin film substrates. Radius 24 has been applied to each cell pattern 22 corner to improve tear strength. Changing the dimensions of cell member 26 can alter the configuration of cell pattern 22. Different physical properties can be imparted along each axis of the film. Referring to FIG. 3B, a perspective view of a machined film 21, tapered cell pattern 22 has been machined into the film to impart porosity, which can support tissue ingrowth. The ability to alter mechanical properties with tapered cell pattern 22 geometry is demonstrated. Manufacturing methods to impart patterns such as cell pattern 22 include, but are not limited to, laser machining, die punching, water jet cutting, and chemical etching. The lasers preferred for creating smooth edges on plastic films include, but are not limited to, $CO_2$, diode ultraviolet, or excimer lasers. An implant having cell pattern 22 is expected to confer benefit to a patient in which it is implanted because of the substantially smooth edges of cell pattern 22.

Figure 4A:
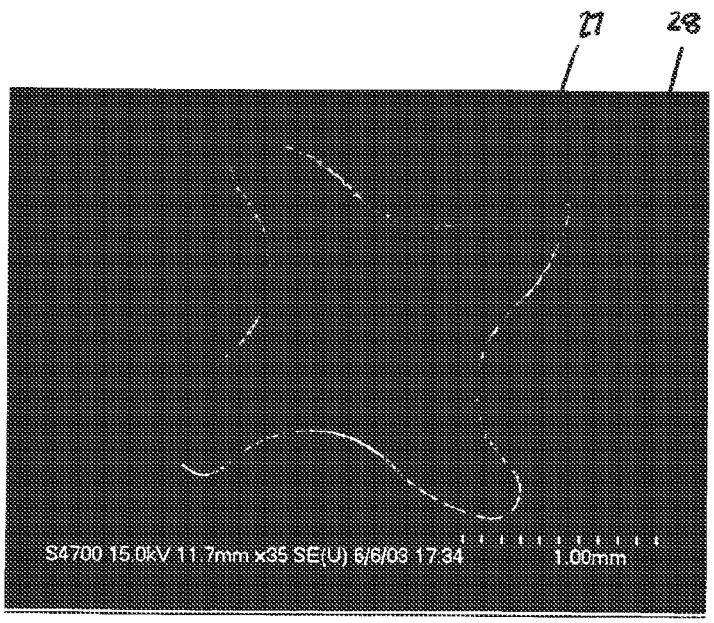
FIGS. 4A and 4B are photomicrographs of an exemplary cell (FIG. 4A; this cell-shape was incorporated in Mesh4) and of the edge of that cell (FIG. 4B).
Figure 4B:
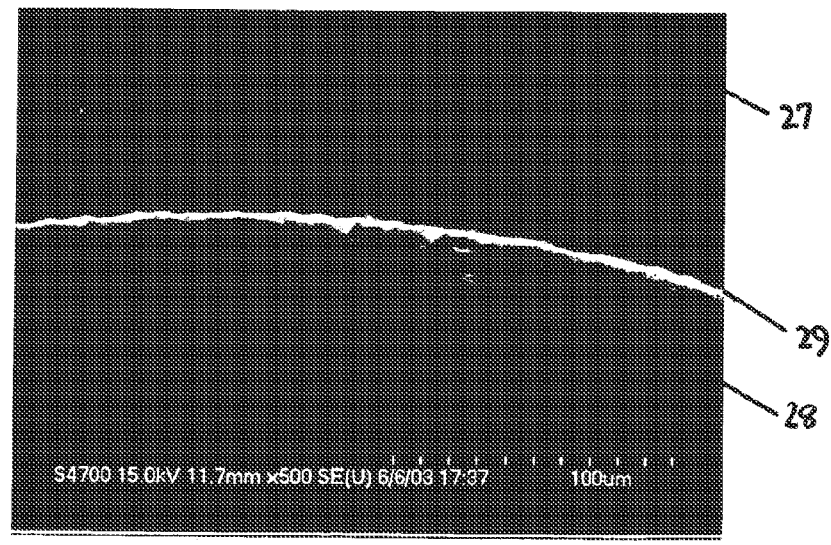

Referring to FIGS. 4A and 4B, cell member 27 was created in biocompatible film 28. Atraumatic edge 29 lies at the interface between cell member 27 and biocompatible film 28. Cell member 27 was created using a 3.0-Watt Avia Q-switched Ultraviolet Laser (Coherent, Inc., Santa Clara, Calif.).

Figure 5:
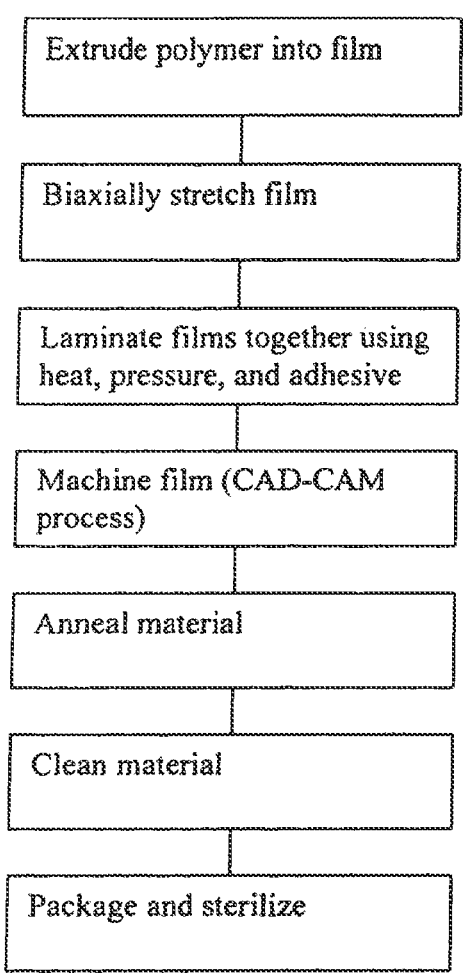
FIG. 5 is a flow chart illustrating some of the steps in a method of producing a soft tissue implant of the invention.

Referring to FIG. 5, a block diagram shows manufacturing, steps for creating a non-woven soft tissue implant. The polymer used to construct the film is extruded using melt or paste extrusion techniques (as noted herein, in alternative methods of the invention, the film can be obtained, rather than made). After extrusion, the mechanical properties (e.g., tensile strength) can be improved through a biaxial stretching process (this is an optional step). Equipment that can be used to carry out this process can be purchased from Bruckner GmbH (Siegsdorf Germany). If desired, the film can be laminated using heat, pressure, or adhesives to further improve the mechanical properties of the implant. Films with properties that may improve an implant (e.g., films with increased tear strength) can be added at this step. A cell pattern (such as one described or illustrated herein) is machined into the film. The film can be annealed at elevated temperatures (e.g., above the glass transition temperature for the polymer within the film) to relieve stresses caused by film stretching and the machining process. The material can then be cleaned, packaged, and sterilized. The packaging material can include instructions for use (i.e., instructions be printed on the packaging material); similarly, instructions can be provided on a separate material.

Referring to FIGS. 6A, 8A, 9A, and 10A, unit cells of Mesh2, Mesh2C, Mesh4, and Mesh3, respectively, are diagrammed. As shown in the legends, Ap=Area of pore;
Pp=perimeter of pore;
t=thickness;
Ac=Area of space in unit cell;
Atop=Ac-As
Abot=Bottom surface area;
Abot=Atop
A5=Area of thickness
At=t(Pg+4(Pp/4))=2t.Pp
Asu=Surface area of a unit cell
Asu=Atop+Abot+At; and
Asurf=Total 3D surface area per 2D area of mesh.

Referring to FIGS. 6B, 8B, 9B and 10B, methods for calculating the surface area ratio of Mesh2, Mesh2C, Mesh4, and Mesh3 are provided in tabular form. A summary of the four nonwoven films, their thickness and surface area ratio are shown in the following Table:

| Product | Thickness (cm) | Surface Area Ratio |
|---|---|---|
| Mesh2 | 0.020 | 0.79 |
| Mesh2C | 0.020 | 0.97 |
| Mesh3 | 0.020 | 0.94 |
| Mesh4 | 0.020 | 0.54 |

Figure 11:
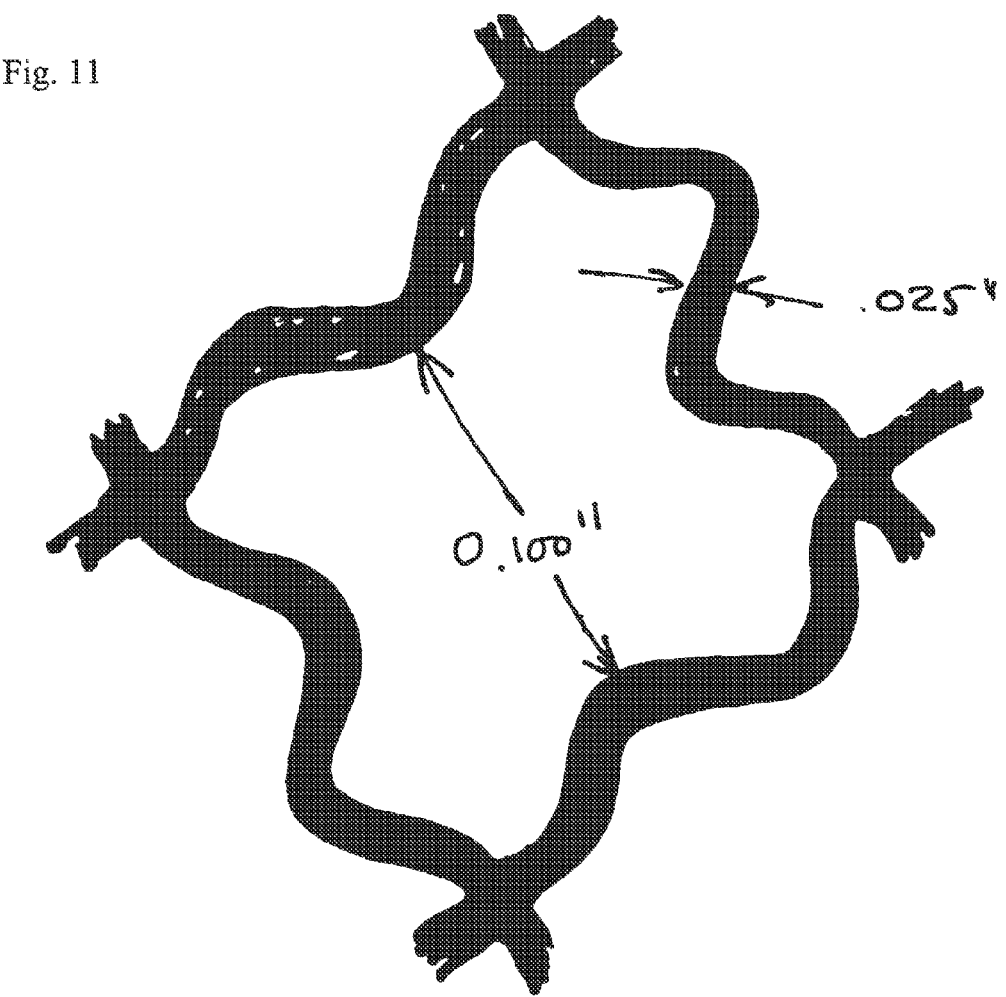
FIG. 11 is an illustration of a cell.

Referring to FIG. 11, an exemplary pore having an opening of 0.100" and a wall thickness of 0.025 inches is shown.

Figure 12:
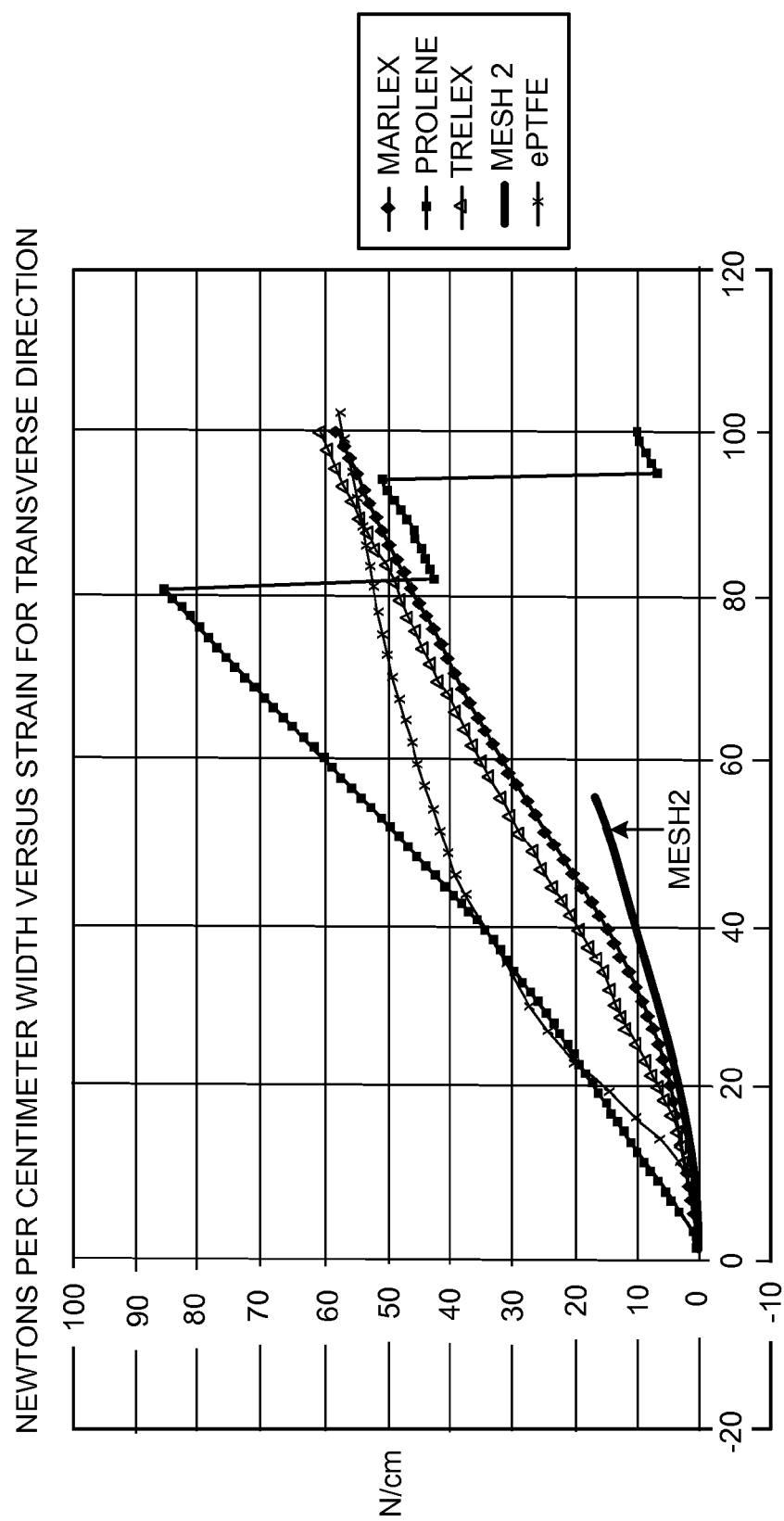
FIG. 12 is a graph showing the percentage strain (x-axis) on various soft tissue implants including Marlex™, Prolene™, Trelex™, Mesh2, and ePTFE.

Referring to FIG. 12, a graph illustrates the percentage strain (x-axis) on various soft tissue implants including Marlex™, Prolene™, Trelex™, Mesh2, and ePTFE.

Figures 6A, 6B:
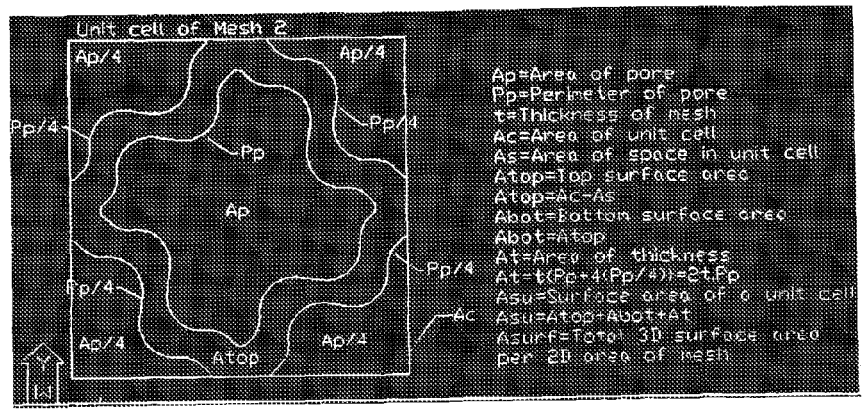
FIGS. 6A and 6B relate to a non-woven soft tissue implant designated Mesh2.

As illustrated by FIG. 3A and FIG. 6A, for example, the cells within a soft tissue implant can be regularly shaped (as are the rectangular cells of FIG. 3A) or irregularly shaped (i.e., they can have an irregularly shaped perimeter, as shown in FIG. 6A, which may or may not be symmetrical). For example, the cell can be of a "regular" shape when it is essentially square, rectangular, or diamond-shaped, or essentially round or oval; the cell(s) can be of an "irregular" shape when at least one of the cell walls contains a sinusoidal element. Moreover, each of the cells in the implant can have a plurality of undulating elements that form a repeating pattern (e.g., the undulations can be in phase with one another). The shape of the cells, their pattern, number, size, etc. can vary as described herein regardless of the film from which the implant is constructed (i.e., the cells can vary as described herein regardless of whether the film is non-porous or microporous; whether the implant contains a single film or multiple films; whether the film contains an absorbable or non-absorbable polymer; whether the implant contains a film to increase tear resistance; etc.).

In any event (regardless of the cellular shape), the length of an opening (i.e., the distance between one part of the cell wall and another (e.g., the distance along the longest axis, the shortest axis, an intermediate axis; the distance between two points that do not define an axis)) can be between about 10 and about 10,000 microns (e.g., about 50-100 (e.g., about 75); about 10-1,000 (e.g., about 500); about 10-2,000 (e.g., about 1,200); about 10-5,000 (e.g., about 2,500); about 10-7,500 (e.g., about 4,500); about 100-1,000 (e.g., about 750); about 500-2,000 (e.g., about 1,750); about 1,000-3,000 (e.g., about 2,100); about 1,000-5,000 (e.g., about 3,500); about 1,500-5,000 (e.g., about 3,750) about 4,000-6,000 (e.g., about 4,750); about 5,000-7,500 (e.g., about 6,500); about 6,000-8,000 (e.g., about 7,200); or about 7,500-10,000 (e.g., about 9,000 microns). In one embodiment, the cells of a soft tissue implant will be about 10-10,000µ; about 1,500-5,000µ; or about 50-100µ (i.e., the length across the longest axis of the cell can be about 100µ, 250µ, 500µ, 1,000µ or 2,000µ. Such implants (e.g., implants in which the longest length of a cellular opening is about 2,000 microns) can be porous enough to permit tissue ingrowth while having mechanical properties (e.g., sufficient strength and flexibility (e.g., an implant flexible along two axes)). One or more of the cells its the plurality within an implant can have essentially the same shape as the cell shown herein as that of Mesh2, Mesh2C, Mesh3, or Mesh4.

Finite element analysis can be used to design a cell or cell pattern that, when incorporated in a soft tissue implant, provides the implant with properties that approximate one or more of the properties of the soft tissue being repaired or replaced. Human skeletal muscle can exert 3-4 kg of tension per square centimeter of cross sectional area. Since many muscles in humans (or other animals, which may also be treated with a soft tissue implant described herein) have a relatively large cross-sectional area, the tension they develop is quite large. The gluteus maximus can exert a tension of 1200 kg, and the quadriceps can exert a tension of 360 kg. This difference is due to varying cross sectional areas. Because areas of the body contain different muscle groups, the non-woven soft tissue implants of the invention can be constructed so that their characteristics (e.g., their strength characteristics) match those of the tissue(s) being replaced or repaired. For example, the soft tissue implant can have force displacement characteristics that do not restrict tissue movement (e.g., that do not restrict the contraction or stretching of a muscle to which the implant is attached) or that restrict such movement to a limited extent. For example, a soft tissue implant can restrict tissue movement by less than 5%, less than 10%, less than 25%, or less than 50%. The force displacement character of a given implant can be calculated by measuring the percentage by which the implant is displaced (e.g., the amount by which it "gives" relative to as resting configuration) under a given force. For example, a soft tissue implant can be distended by about 25% (or more (e.g., 30, 35, 40, 45, 50% or more)) at 16 N/cm (see FIG. 12). The number, shape, and arrangement of the plurality of cells and the thickness of the implant can be varied to impart force displacement characteristics that approximate those of the structure being repaired.

As noted above, the films can be made from a variety of polymers, including absorbable polymers. Where the implant contains more than one absorbable (e.g., bioresorbable) film, the rate at which on film (e.g., a first film) is resorbed within a body can be different from the rate at which another film (e.g., a second film) is resorbed. As with other bi-layer or multi-layer implants of the invention, a surface of the first film can adhere to a surface of the second film, and multi-layer implants can include a film that increases tear resistance (e.g., a porous biocompatible film).

A soft tissue implant can also be defined by measured parameters such as the area of a cell (or pore; Ap (see the size ranges above), its perimeter (Pp), the area of a cell "unit" (Ac), and the surface area ratio (Asurf), which is preferably less than 1.5. A method for calculating Asurf is shown in FIG. 6B, for example. Asurf is calculated by dividing Asu (the 3D surface area of a unit cell) by the area of the unit cell (Ac). Asu is determined by adding the top surface area (Atop), the bottom surface area (Abot; which can equal the top surface area), and the area of thickness (At). These values, in turn, can be found as follows: Atop is the difference between the area of a unit tell (Ac) and the area of space in a unit cell (As); Abot can equal Atop; and At equals the thickness of the film multiplied by (Pp+4(Pp/4)). Lastly, As is equal to Ap plus 4(Ap/4) (which is equal to 2Ap).

The methods of making a soft tissue implant include those described above as well as the following. An implant can be made by a method that includes the steps of extruding a biocompatible polymer into a film and forming a plurality of cells in the film. The film can be of a thickness described above and have the material content described above, and the cells can have the characteristics of any of those described above. As noted, the extrusion process can be, for example, a melt or paste extrusion process, and the cells can be formed by, for example, laser ablation or machining (e.g., die punching). A soft tissue implant having more than one layer can be made by a method that includes the steps of (a) extruding a first biocompatible polymer to form a first film; (b) extruding a second biocompatible polymer to form second film; (c) attaching the first film to the second film to produce a soft tissue implant and (d) forming pores in the soft tissue implant. Alternatively, a multi-layer implant can be made by a method including the steps of (a) extruding a first biocompatible polymer to form a first film; (b) forming pores or cell patterns in the first film; (c) extruding a second biocompatible polymer to form a second film; (d) forming pores in the second film; and (e) attaching the first film to the second film to produce a soft tissue implant. As for single-layer implants, the films can be of a thickness described above and have the material content described above, and the cells can have the characteristics of any of those described above. Any of the soft tissue implants made by these methods can be further processed (e.g., their edges can be modified to facilitate tissue placement and/or their shape can be changed (by, for example, stretching)). The implants can also be cleaned and/or sterilized and packaged, with or without instructions for use. Any of the soft tissue implants made by these methods can be used to repair, or in the course of repairing, a damaged tissue in a body (including, but not limited to, a human body).

Medical implant applications for the soft tissue implant technology described above may include, but are not limited to, plastic reconstruction, urinary stress incontinence, hernia repair, gastric banding, and chest wall reconstruction. Accordingly, the methods of the invention include methods of treating a patient who has sustained an injury to a tissue, independent of the source of the injury (i.e., the injury could arise from a traumatic injury, including an accidental injury or a surgical incision, or the injury may be associated with a disease, disorder, or condition). The method can include exposing, preferably under sterile conditions, the injured tissue (e.g., a muscle, muscle group, or other tissue such as the intestine, liver, or kidney), and administering a soft tissue implant to the tissue. The implant can be further secured to the tissue by one or more sutures, staples, or other fasteners. Alternatively, or in addition, the implant can be secured by an adhesive. The surgical incision through which the implant was inserted can then be closed. The physician or surgeon performing the operative procedure can select an appropriate implant. For example, it will be readily apparent what size implant is required (generally, the implant should be large enough to cover the affected part of a tissue). Similarly, the physician or surgeon can choose a non-absorbable implant when appropriate. For example, one may select a non-absorbable soft tissue implant for indications such as hernia repair that require long-term durability and strength. Alternatively, one may select an absorbable soft tissue implant for indications such as tissue augmentation during plastic reconstruction when one wants to avoid the potential complications associated with a permanent implant. Tissue-based materials are best suited for indications such as pelvic slings that require materials less prone to erosion into adjacent tissue structures.

In other methods, the soft tissue implant can be produced in more three-dimensional forms for certain indications, such as the plug and patch procedure for inguinal hernia repair. A three dimensional structure can be machined using a laser system incorporating a third axis for micromachining. Alternatively, the nonwoven soft tissue implant could be thermoformed into a three-dimensional shape after machining.

The product designs may also be suitable for non-medical device applications. Non-medical applications may include diagnostic testing, in biotechnology or other research, in automotive, electronics, aerospace, and home and commercial appliances.

A number of embodiments of the invention have been described. Nevertheless, it will be understood that various modifications may be made without departing from the spirit and scope of the invention.

EXAMPLES

Example 1

Figure 7A:
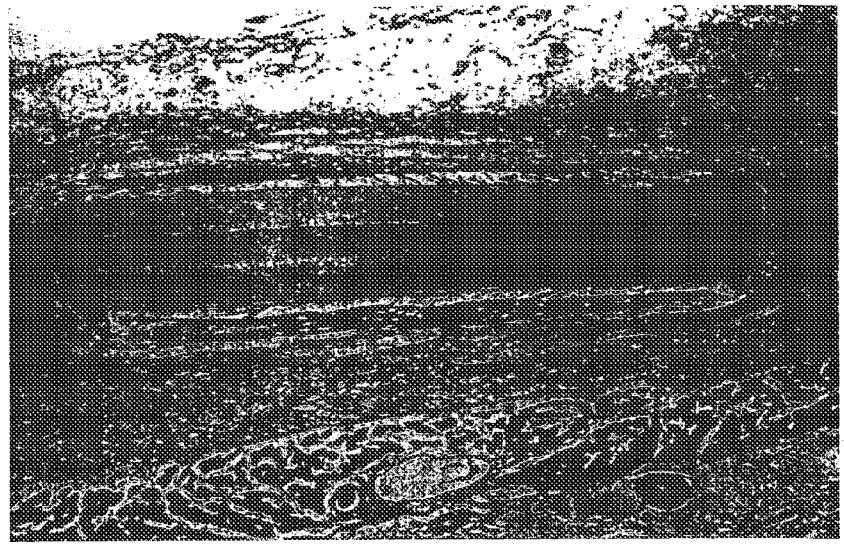
FIGS. 7A and 7B are photomicrographs.
Figure 7B:
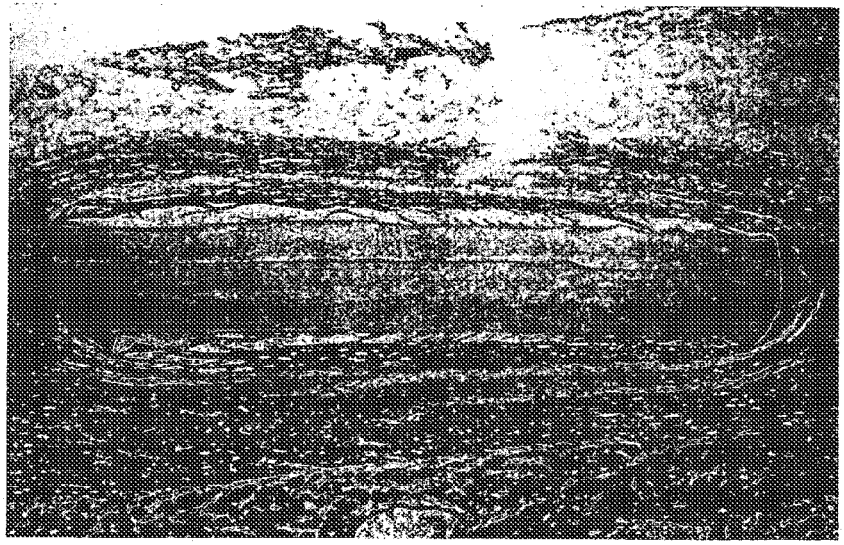
Figures 8A, 8B:
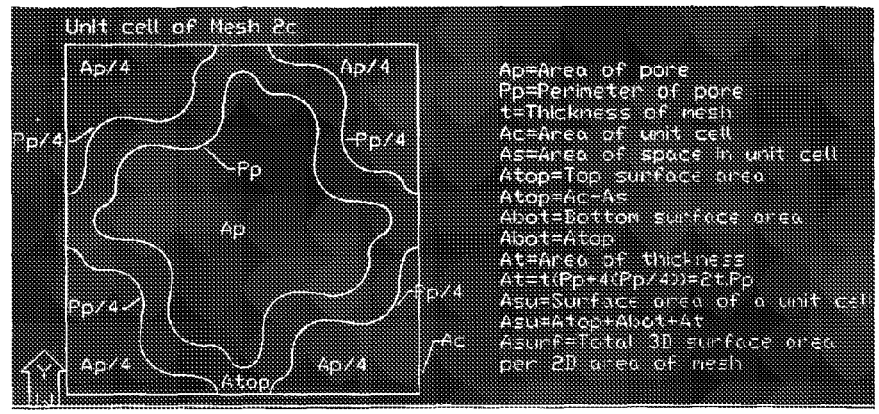
FIGS. 8A and 8B relate to a non-woven soft tissue implant designated Mesh2C.
Figure 9A:
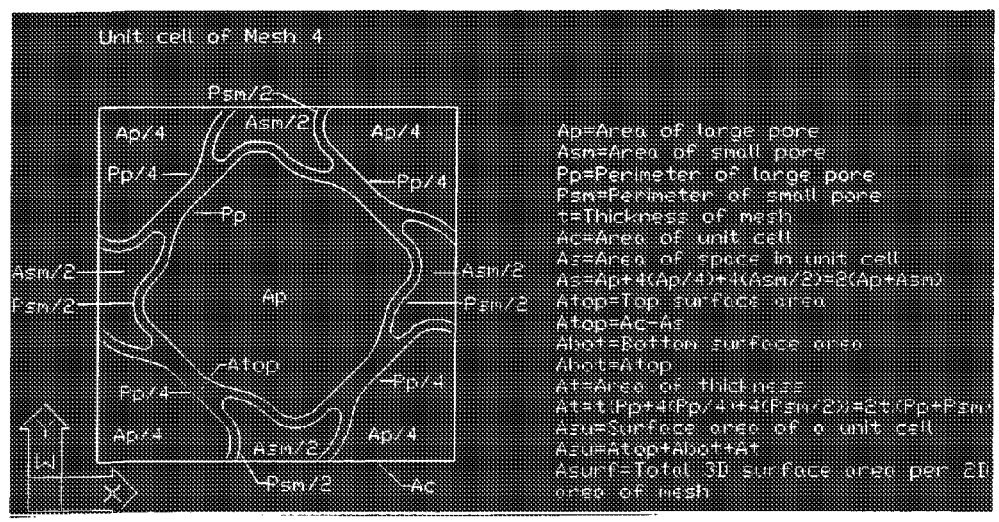

A non-woven soft tissue implant was constructed using biaxially-oriented polymer films. The film is stretched in both the machine and transverse directions (relative to the extrusion direction) to orient the polymer chains. The stretching process can take place simultaneously or sequentially depending on the equipment that is available. The base film was Syncarta™ (AET Films, Peabody, Mass.). The base film was machined into Mesh Design 2 ("Mesh2") using a 3.0-Watt Avia Q-switched Ultraviolet Laser produced by Coherent, Inc. (Santa Clara, Calif.). The design of a cell of the non-woven soft tissue implant is shown in FIG. 6A. The finished product was implanted, using standard surgical techniques, in the subcutaneous tissue of rats for 7, 14, and 28 days. Following sacrifice and retrieval of the specimens, histological evaluation was carried out to evaluate the inflammatory and wound healing response. Histology sections were obtained and stained with Haematoxylin and Eosin for cellularity of the implant site and Masson's Trichrome stain was used to evaluate the extent of fibrous capsule formation. The findings over a 28-day period indicate that the nonwoven soft tissue implant is biocompatible and undergoes a normal resolution of the inflammatory response, secondary to surgical injury, and development of a normal foreign body reaction at the material/state interface with fibrous capsule formation surrounding the entire implant and within the holes of the material. The results of histological analyses are shown in FIGS. 7A and 7B.

Example 2

A non-woven soft tissue implant was constructed using biaxially-oriented polymer films. Two base films were used. The first film was a two-side sealable material OPB 95 (AET Films, Peabody, Mass.). The second film was a one-side sealable material AQS 90 (AET Films). Six sheets of the first film were placed between two sheets of the second film with the sealable side of the second in contact with the first film set. The sheet assembly was brought to 145° C. at 400 PSI of constant pressure for 60 minutes under vacuum. The laminated assembly was machined into designs Mesh2 and Mesh4 (see FIGS. 6A and 9A, respectively) using a 3.0-Watt Avia Q-switched Ultraviolet Laser produced by Coherent, Inc. (Santa Clara, Calif.).

Example 3

A non-woven soft tissue implant was constructed using biaxially-oriented polymer films. Two base films were produced. The first film comprised a three-layer extrusion in an A-B-A form. The "A" layer was made up from PKS409 resin (Solvay Polyolefins Europe, Brussels, Belgium) and the "B" layer was made up from HC312BF resin (Borealis Group, Kongens Lyngby, Denmark). The layers were melt extruded and oriented using a stenter film process. The film was oriented in the machine direction at a 5:1 ratio and in the transverse direction at a 10:1 ratio. The thickness of the film after stretching was 24μ. The second film included a three-layer extrusion in an A-A-B form. The "A" layer was made up from HC312BF and the "B" layer was made from PKS409. The layers were melt extruded and oriented using a stenter film process. The film was oriented in the machine direction at a 5:1 ratio and in the transverse direction at a 10:1 ratio. The thickness of the film after stretching was 23μ. Six sheets of the first film were placed between two sheets of the second film with the "B" side in contact with the first film set. The sheet assembly was brought to 145° C. at 400 PSI of constant pressure for 60 minutes under vacuum. The laminated assembly was machined into the design Mesh2C (see FIG. 8A) using a 3.0-Watt Avia Q-switched Ultraviolet Laser produced by Coherent, Inc. (Santa Clara, Calif.). In addition, cell patterns of design Mesh4 were created in the same assembly using a die punch produced by Elite Tool & Die (Smithstown, Ireland). Surface area ratios for the cell patterns in the produced films were calculated and are shown in the Table above.

Example 4

Polyaryletherketone (PEEK; Invibio Inc., Lancashire, UK) is a polymer that has properties making it useful as an implant material for devices such as spine cages, bone screws, orthopedic stems, and dental implants. PEEK exhibits a desirable combination of strength, stiffness, and toughness, and it is biocompatible. Accordingly, a soft tissue implant was constructed using PEEK material. Westlake Plastics (Lenni, Pa.) supplies PEEK polymer films that range from about 0.001 to about 0.029 inches thick. These films can be used to fabricate biocompatible implants with lower profiles than commercially available textile based products. A film made of 0.005 inch PEEK polymer was machined using an ultraviolet laser (more specifically, a 3.0-Watt Avia Q-switched Ultraviolet Laser (Coherent, Inc., Santa Clara, Calif.)) into the pattern shown in FIG. 6A using a CAD-CAM process. FIG. 4B shows a highly magnified image of a cell pattern edge created using the laser machining process. This soft tissue implant has an implant surface area ratio of 0.79, which reduces the amount of material available to provoke a foreign body reaction. In addition, the implant had a smooth surface with a low coefficient of friction.

Example 5

Polytetrafluoroethylene (PTFE; Bard Vascular Systems (Tempe, Ariz.)) polymer also has properties that allow it to be used, as described herein, as an implant material for, for example, vascular grafts and patches. PTFE can be processed into a microporous form using an expansion procedure. Like PEEK, expanded PTFE is strong, flexible, and biocompatible.

Example 6

Figure 10A:
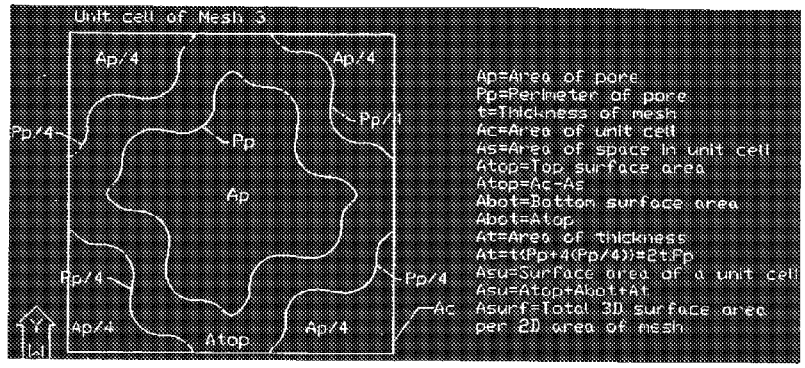

Yet another non-woven soft tissue implant was constructed using a biaxially-oriented polymer film. The film is stretched in both the machine and transverse directions (relative to the extrusion direction) to orient the polymer chains. As noted above, the stretching process can take place simultaneously or sequentially depending on the equipment that is available. The base film was Syncarta™ (AET Films, Peabody, Mass.). The base film was machined into Mesh Design 3 ("Mesh3") using a 3.0-Watt Avia Q-switched Ultraviolet Laser produced by Coherent, Inc. (Santa Clara, Calif.). The design of a cell of the non-woven soft tissue implant is shown in FIG. 10A.

Further embodiments are within the scope of the following claims.

What is claimed is:

1. A non-woven soft tissue implant comprising a first porous biocompatible film having a plurality of unit cells and a second porous biocompatible film having a plurality of unit cells, the thickness of the implant being less than 0.015 inches,
   wherein each unit cell comprises a pore and a portion of the film extending around the perimeter of the pore to define the pore; and
   wherein the implant has a surface area ratio (Asu/Ac) of less than 1.5,
   wherein
   Asu=the three dimensional surface area of the unit cell, and
   Ac=the two dimensional area of the unit cell.

2. The non-woven soft tissue implant of claim 1, wherein the first film and the second film consist of the same material or materials.

3. The non-woven soft tissue implant of claim 1, wherein the first film and the second film consist of different materials.

4. The non-woven soft tissue implant of claim 3, wherein the first film or the second film includes a bioresorbable material and the rate at which the first film is resorbed within a body is different from the rate at which the second film is resorbed within the body.

5. The non-woven soft tissue implant of claim 1, wherein the first film or the second film comprises a cell having a diameter, measured along the longest axis of the cell, of 10 microns to 10,000 microns.

6. The non-woven soft tissue implant of claim 1, further comprising a film that increases tear resistance, wherein the film is located between the first film and the second film.

7. The non-woven soft tissue implant of claim 1, wherein the plurality of cells in the first biocompatible film or the plurality of cells in the second biocompatible film comprises a cell pattern containing a sinusoidal element.

8. The non-woven soft tissue implant of claim 1, wherein each film comprises a polymer or a copolymer having biaxially oriented chains.

9. The non-woven soft tissue implant of claim 1, wherein the implant has a surface area ratio of less than 1.0.

10. The non-woven soft tissue implant of claim 1, wherein the implant has a surface area ratio of less than 0.8.

11. The non-woven soft tissue implant of claim 1, wherein the implant has a surface area ratio of less than 0.5.

12. The non-woven soft tissue implant of claim 1, having a smooth surface and at least one atraumatic edge.

13. The non-woven soft tissue implant of claim 1, wherein one or both of the first and second films has a thickness of between 0.001 to 0.014 inches.

14. The non-woven soft tissue implant of claim 1, distended by at least 25% at a force borne by a tissue.

* * * * *